(12) United States Patent
Tequi et al.

(10) Patent No.: US 8,916,726 B2
(45) Date of Patent: Dec. 23, 2014

(54) METHOD FOR THE PREPARATION OF LOW OVERBASED ALKYLTOLUENE SULFONATE

(75) Inventors: Pierre Tequi, Nointot (FR); Curt B. Campbell, Hercules, CA (US); Gilles P. Sinquin, Saint Martin du Manoir (FR); Christine Boemare Gandon, Montivilliers (FR); Kyle J. Frederic, Marrero, LA (US); Eugene E. Spalla, Fairfield, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 14/001,346

(22) PCT Filed: Mar. 20, 2011

(86) PCT No.: PCT/US2011/030566
§ 371 (c)(1),
(2), (4) Date: Aug. 23, 2013

(87) PCT Pub. No.: WO2012/134464
PCT Pub. Date: Oct. 4, 2012

(65) Prior Publication Data
US 2014/0081043 A1  Mar. 20, 2014

(51) Int. Cl.
*C07C 309/00* (2006.01)
*B01J 19/00* (2006.01)
*C07C 2/66* (2006.01)
*C07C 303/14* (2006.01)
*C07C 303/06* (2006.01)
*C07C 303/32* (2006.01)
*B01J 8/02* (2006.01)

(52) U.S. Cl.
CPC ...... *C07C 303/06* (2013.01); *B01J 2219/00166* (2013.01); *B01J 2219/00231* (2013.01); *C07C 2529/08* (2013.01); *B01J 19/0013* (2013.01); *B01J 2219/00186* (2013.01); *C07C 2/66* (2013.01); *B01J 19/0033* (2013.01); *B01J 2219/00202* (2013.01); *C07C 2529/70* (2013.01); *C07C 303/14* (2013.01); *C07C 303/32* (2013.01); *B01J 8/02* (2013.01)
USPC .............................. 562/45; 562/98

(58) Field of Classification Search
None
See application file for complete search history.

(56) References Cited

U.S. PATENT DOCUMENTS

| | | | |
|---|---|---|---|
| 4,235,810 A | 11/1980 | Osseelet et al. | |
| 4,259,193 A | 3/1981 | Laurent et al. | |
| 4,452,708 A * | 6/1984 | Aldrich et al. | 507/259 |
| 4,682,653 A | 7/1987 | Angstadt | |
| 5,922,922 A | 7/1999 | Harris et al. | |
| 5,939,594 A | 8/1999 | Le Coent | |
| 6,337,310 B1 | 1/2002 | Campbell | |
| 6,476,282 B1 | 11/2002 | Le Coent | |
| 6,479,440 B1 | 11/2002 | Le Coent | |
| 6,551,967 B2 | 4/2003 | King | |
| 7,109,141 B2 | 9/2006 | Campbell et al. | |
| 7,563,937 B2 | 7/2009 | Harris et al. | |
| 2005/0250970 A1 | 11/2005 | Harris et al. | |
| 2007/0021317 A1 | 1/2007 | Le Coent et al. | |
| 2008/0113884 A1 * | 5/2008 | Campbell et al. | 507/259 |
| 2008/0119378 A1 | 5/2008 | Gandon et al. | |
| 2009/0209778 A1 | 8/2009 | Campbell et al. | |

OTHER PUBLICATIONS

PCT/US2011/030566. International Search Report, 3 pages.

* cited by examiner

Primary Examiner — Karl J Puttlitz
(74) Attorney, Agent, or Firm — Joseph P. Foley

(57) ABSTRACT

Disclosed is a method for improving filtration in the preparation of an alkaline earth metal alkyltoluene sulfonate concentrate by selectively controlling the meta, ortho, para isomer distribution of the alkyl group of the alkyltoluene produced by the process comprising alkylating toluene with at least one isomerized normal alpha olefin, having from about 18 to about 30 carbon atoms and having from 20% to 100% branching in an alkylation process which includes monitoring % isomer formation and adjusting an alkylation process parameter in order to provide a target specified isomer content of less than 38% meta-isomer content; and thereafter sulfonating and neutralizing to produce a low base number sulfonated alkyltoluene concentrate having a Base Number of about 2 to 60 (ASTM D 2896).

14 Claims, No Drawings

METHOD FOR THE PREPARATION OF LOW OVERBASED ALKYLTOLUENE SULFONATE

FIELD OF INVENTION

The present invention relates to an improved method for the preparation of low overbased alkyltoluene sulfonates derived from isomerized normal alpha olefins by maintaining isomer selectivity.

BACKGROUND

Sulfonates, particularly calcium, barium or magnesium overbased sulfonates are widely used as additives for lubricating oils. The term "overbased" is used to describe sulfonates containing an amount of metal in excess of that required to react with the sulfonic acid from which the sulfonate is obtained. These overbased sulfonates are used as detergents in the lubricating oil where their basicity neutralizes acids which develop in the crank cases of engines during operation.

Sulfonates are generally obtained from monoalkylates of aromatics, commonly benzene. The process for preparation of alkyl aromatics is known and is typically conducted by the catalytic alkylation of aromatic hydrocarbons with alkyl chain being branched or straight chain hydrocarbons typically greater than 16 carbon atoms for oil solubility. Common alkyl groups are olefins such as normal alpha olefins, branched-chain olefins, isomerized normal alpha olefins which are partially branched, or mixtures thereof. The alkylated aromatic hydrocarbons can then be converted into corresponding sulfonic acids which can be further converted into alkylated aromatic sulfonates.

Various chemical aspects of the alkylated aromatic hydrocarbon have been known to influence the physical, chemical and performance properties of the corresponding sulfonate. These chemical aspects have included: the position along the alkyl chain of the attachment to the aromatic ring, and the amount of heavy alkylate which is present in the alkylaromatic hydrocarbon. Heavy alkylate may be composed of, but are not limited to, mono-alkylates of oligomerized olefins, di-alkylated species, and oligomerized olefin species.

U.S. Pat. No. 4,235,810 discloses alkyl aromatics prepared by alkylation with a mixture of straight and branched chain olefins containing 16 to 30 carbon atoms preferably form oligomers of propylene.

U.S. Pat. No. 4,259,193 discloses overbased alkaline earth metal mono-alkyl ortho-xylene in which the alkylaryl moiety is a mono-alkyl ortho-xylene or a mono-alkyl toluene and the alkyl group contains 15 to 40 carbon atoms. The alkyl group may be straight chain or branched. Oligomers of propylene may be used for the alkyl group. In the examples, the overbased sulfonates have a Total Base Number of 300.

U.S. Pat. No. 6,551,967 discloses low overbased calcium sulfonates wherein the alkylaryl moiety is alkyltoluene or alkylbenzene in which the alkyl group is a 15 to 21 carbon branched chain alkyl group derived from a propylene oligomer prepared by the process by reacting an alkyltoluene sulfonic acid with an active source of alkaline earth metal in the presence of solvent wherein the solvent does not comprise an organic solvent.

US2008/0119378 discloses formulations, methods of making, and methods of using a functional fluid to achieve and maintain optimal frictional characteristics in machines housing that fluid, where the functional fluid comprises a friction-modifying amount of an alkyl toluene sulfonate salt or a mixture of alkyl toluene sulfonate salts.

US2007/0021317 discloses detergent mixtures of alkyl aryl sulfonates of alkaline earth metals obtained by sulfonating mixtures of heavy linear alkylbenzene and alkyltoluene. The heavy linear alkylbenzene preferred is comprised of a low meta-dialkyl benzene with the para-dialkylbenzene being the predominant species. The sulfonates exhibit improved stability and compatibility.

U.S. Pat. No. 7,109,141 discloses alkylated aromatic compositions, zeolite catalyst compositions and processes for making them. The catalyst compositions comprise zeolite Y and mordenite zeolite having a controlled macropore structure.

U.S. Pat. No. 5,939,594 and U.S. Pat. No. 6,476,282 disclose the preparation of a superalkanized alkylaryl sulfonates of alkaline earth metal, derived from toluene. The alkyl group of the alkylaryl sulfonate contains between 14 to 40 carbon atoms and the aryl sulfonate radical of alkaline earth metal is fixed in a molar proportion comprised between 0 and 13% in positions 1 or 2 of the linear alkyl chain. The catalysts used in the alkylation reaction are conventional catalysts which include hydrofluoric acid, boron fluoride, aluminum chloride or an acid activated clay.

U.S. Pat. No. 4,682,653 discloses a method for the recovery of oil from a subterranean reservoir which comprises injecting steam and a dialkylaromatic sulfonate surfactant into the reservoir, and producing oil displaced by said surfactant and steam, said surfactant being comprised of a mixture of para- and meta-isomers of said dialkylaromatic sulfonate, wherein the amount by weight of the para-isomer in the mixture has been increased relative to the amount of meta-isomer sufficient to provide an increase in the hydrolytic stability of said mixture.

U.S. Pat. No. 6,479,440 discloses highly overbased alkaline earth alkylaryl sulfonates wherein the alkyl chain is a linear chain that contains between 14 and 40 carbon atoms, wherein the mole % of the aryl-sulfonate radical fixed on position 1 or 2 of the linear alkyl chain is between 13 and 30%. Such an alkaline earth alkylaryl sulfonate has improved compatibility, solubility and foaming performances while having low color and no skin formation.

U.S. Pat. No. 5,922,922 discloses a process for isomerizing a normal alpha olefin in the presence of an acidic catalyst having a one-dimensional pore system, and then using of the isomerized olefin to alkylate aromatic hydrocarbons in the presence of a second acidic catalyst, which can be zeolite Y.

U.S. Pat. No. 7,041,863 discloses preparation of an alkylation catalyst and a process for alkylating aromatic hydrocarbons using a specific Y-zeolite catalyst. Further discloses the preparation of a carbonated overbased alkylated benzene sulfonate derived from an isomerized olefin.

US2005/0250970 discloses a zeolite Y catalyst having a controlled macropore structure and a process for preparing the catalyst composite. The catalyst composite exhibits reduced deactivation rates during the alkylation process, thereby increasing the life of the catalyst.

Also disclosed is a process for the preparation of carbonated, overbased aromatic sulfonates, which processes comprise alkylation, carbonation of aromatic hydrocarbons with one or more olefins.

U.S. Pat. No. 7,563,937 discloses a zeolite Y catalyst having a controlled macropore structure and a process for preparing the catalyst composite. The catalyst composite exhibits reduced deactivation rates during the alkylation process, thereby increasing the life of the catalyst. Also disclosed is a process for the preparation of carbonated, overbased aromatic sulfonates, which processes comprise alkylation, carbonation of aromatic hydrocarbons with one or more olefins.

SUMMARY

Disclosed is a method for improving filterability in the preparation of an alkaline earth metal alkyltoluene sulfonate concentrate which comprises (a) monitoring the isomeric distribution of at least one alkyltoluene produced by alkylating toluene with at least one isomerized normal alpha olefin, said isomerized normal alpha olefin having from about 18 to about 30 carbon atoms and having from 15 wt % to 100 wt % branching; (b) adjusting at least one alkylation process parameter in order to provide a target isomer distribution having a 2-tolyl C24 isomer content of less than 38 wt % meta, relative to the total 2-tolyl C24 isomer content; (c) sulfonating the alkyltoluene to produce an alkyltoluene sulfonic acid; (d) neutralizing the alkyltoluene sulfonic acid with a source of an alkaline earth metal to provide a neutralized alkyltoluene sulfonate concentrate having a base number of from about 2 to about 60. In one aspect, the alkylation process parameter is selected from the group consisting of adjusting the feed temperature of at least one reactant, adjusting the charge mole ratio of the reactants, and adjusting the weight hourly space velocity of the feed. More particularly, the process parameter comprises reducing the feed temperature of at least one reactant. Other suitable process parameters may comprise adjusting the charge mole ratio of the reactants; in another aspect the parameter may be adjusting the weight hourly space velocity of the feed.

In a preferred aspect, the alkylation process is a continuous process with dynamic monitoring of the isomer distribution. In this regard, a suitable alkylation process is conducted in a fixed bed catalytic reactor where samples may be taken as periodic samples or in one embodiment more continuous and inline. Typically, samples are taken after process parameter adjustments and periodically over the life of the catalyst. Thus, the monitoring of the isomer distribution and the adjusting of the process condition are dynamic process conditions. The samples are measured for the isomer distribution and compared to a desired target set point for the isomer distribution; if outside the desired values then an alkylation process parameter is selected and adjusted. The process is repeated until the target isomer distribution is achieved. In one aspect, an alkylation process parameter is selected and adjusted to modify a temperature profile in the fixed bed catalytic reactor.

In one embodiment, the alkylation process parameter is adjusted in order to provide a target isomer distribution having a 2-tolyl C24 isomer content of about 18 wt % to about 37 wt % meta content, relative to the total 2-tolyl C24 isomer content. More particularly, the alkylation process parameter is adjusted in order to provide a target isomer distribution having a 2-tolyl C24 isomer content of about 20 wt % to about 30 wt % meta, relative to the total 2-tolyl C24 isomer content. In this regard, the 20 wt % to 30 wt % meta content can further be described as having a target isomer distribution having a 2-tolyl C24 isomer content of about 20 wt % to about 45 wt % ortho, relative to the total 2-tolyl C24 isomer content.

In yet a further embodiment the alkylation process parameter is adjusted in order to provide a target isomer distribution having a 2-tolyl C24 isomer content of about of 20-35 wt % meta-, 25-40 wt % ortho-, and 35-50 wt % para-isomer content relative to the total 2-tolyl C24 isomer content. This isomer distribution which thereafter having been sulfonated and neutralized, has been shown to be gel free or having <0.1 vol % gel and having a filtered sediment<0.2 vol %.

In a preferred aspect, the isomerized normal alpha olefin is characterized as having less than 35% branching. In a further aspect, the isomerized normal alpha olefin can be characterized as having greater than 70 wt % from C20 to C24 carbon atoms.

In another aspect, disclosed is a method for improving filtration in the preparation of an alkaline earth metal alkyltoluene sulfonate concentrate by selectively controlling the meta, ortho, para isomer distribution of the alkyl group of the alkyltoluene produced by the process comprising alkylating toluene with at least one isomerized normal alpha olefin, having from about 18 to about 30 carbon atoms and having no greater than about 30 wt % branching in an alkylation process which includes monitoring % isomer formation and adjusting an alkylation process parameter in order to provide a target specified isomer content of 20-35 wt % meta-, 25-40 wt % ortho-, and 35-50 wt % para-isomer content; and thereafter sulfonating and neutralizing to produce a low base number sulfonated alkyltoluene concentrate having a Base Number of about 2 to 60 (ASTM D 2896).

DETAILED DESCRIPTION

Methods of making calcium sulfonates derived from monoalkylated toluene using acid catalysts are known in the art. However, it has been discovered that the processes for preparing low overbased calcium alkyltoluene sulfonates from isomerized normal alpha olefins, using solid acid alkylation catalysts, at times resulted in an undesirable product which contains gel. The formation of gel is different but somewhat related to sediment levels. The formation of this gel is generally accompanied by a very slow filtration rate and increased sedimentation which increases processing times and/or makes the resulting product commercially unattractive.

The present process is directed in part to improving the filterability of the low overbased calcium alkyltoluene sulfonate by carefully controlling the isomer selectivity thereby curtailing formation of a gel. Alkylation of toluene produces a variety of isomeric monoalkylated toluene; which include but are not limited to meta-alkyltoluene, ortho-alkyltoluene and para-alkyltoluene. More particularly it was determined that by controlling the alkylation process, the positional attachment of the isomerized normal alpha olefin group to the aromatic ring relative to the methyl group of toluene can be altered. Heretofore, the isomer distribution was unknown to effect the formation of the gel and/or improve filtration rates.

Through identification by chromatography, it has been discovered that the low overbased calcium sulfonates derived from alkyltoluene comprising an average meta-isomer content of less than 38% meta isomer content have reduced susceptible to gel formation and filtered sediment of less than 0.2 vol % per ASTM D2273. Isomer content is determined based upon %-isomer 2-tolyl C24 relative to the total 2-tolyl C24 isomer. Calcium sulfonates derived from alkyltoluene having higher relative meta content, demonstrated gel and higher filtered sediment properties which make them not commercially viable. More particularly through identification by chromatography, it has been discovered that the low overbased calcium sulfonates derived from alkyltoluene comprising an average meta-isomer content of about 18-37 wt %, an average para-isomer content of about 35-50 wt % and an average ortho-isomer content of about 25-40 wt % did not result in gel formation of the final product (wherein the % is a weight percent based upon the total).

It has also been discovered that the % isomer formation of the alkyltoluene may be dependent upon the current activity of the acid catalyst and degree of catalyst use/fouling, therefore the ratios of each isomer will vary at different stages in the life cycle of the catalyst such that process conditions require dynamic adjustment if the meta, and in a further aspect the meta/ortho/para, alkyltoluene content is to remain in a predetermined ratio. Accordingly, the isomer selectivity distribution may be monitored and alkylation process conditions can be adjusted to effectuate the target isomer distribution. For example, when the catalyst is fresh or freshly regenerated, and more active, lower feed temperatures may be required to obtain the desired % isomer distribution for the alkyltoluene. As the catalyst becomes less active, due to fouling and cracking, slightly higher temperature may be required to obtain the desired isomer distribution of the alkyltoluene. The toluene/olefins charge mole ratio "CMR" can also be modified among other process conditions. Thus, an aspect of the present invention is directed to dynamically changing an alkylation process variable to achieve the target isomer distribution.

It has been further discovered that the isomer contents of the alkyltoluene can be maintained within the preferred ranges by selecting modifications to the catalyst type or by monitoring % meta-, and in a different aspect the meta- para- and ortho-, isomer formation during the alkylation and then modifying various process parameters in order to achieve optimal temperature profile in the fixed bed catalytic reactor to obtain the desired ratios of each isomer. This desired isomer distribution result is also achievable by blending two batches of alkyltoluene with a different distribution of isomers in order to achieve the desired ratios prior to making the low overbased calcium sulfonates derived from alkyltoluene. In another aspect, the low overbased calcium sulfonates derived from alkyltoluene are prepared and mixed such that the mixture comprises an average meta-isomer content of about 18-37 wt %, average para-isomer content of about 35-50 wt % and average ortho-isomer content of about 25-40 wt %, in this aspect at least one low overbased calcium alkyltoluene sulfonate is outside of the targeted meta, ortho, para isomer distribution. Thus, for example, one may prepare an isomerized normal alpha olefin wherein said olefin is characterized as having from about 18 to about 30 carbon atoms and having from 15% to 100 wt % branching and thereafter prepare a first alkyltoluene with a meta/ortho/para isomer distribution and prepare at least one addition alkyltoluene with a different meta/ortho/para isomer distribution and mixing a portion of said first alkyltoluene with a portion of at one additional alkyltoluene such that the mixture provides a target specified isomer content of 18-37 wt % meta-, 25-40 wt % ortho-, and 35-50 wt % para-isomer content. The alkyltoluene may be thereafter sulfonated and neutralized according to the steps described herein. In an alternative aspect, the first alkyltoluene of above may be sulfonated and the second alkyltoluene of above may be sulfonated and thereafter be mixed together such that the alkyltoluene sulfonic acid mixture provides a target specified isomer content of 18-37 wt % meta-, 25-40 wt % ortho-, and 35-50 wt % para-isomer content. The alkyltoluene sulfonic acid mixture may further neutralized and filtered as described herein.

It is desirable that additives in lubricating oil compositions be relatively free of gel and sediment. In this regard, it is particularly preferred to have low overbased calcium alkyltoluene sulfonates having a filtered sediment of <0.2 vol %. Therefore, the present invention is directed to the discovery of an improved method of making low overbased calcium alkyltoluene sulfonates.

Isomerization of NAO (Normal Alpha Olefin)

The isomerized olefins of the invention can be produced by isomerization of normal alpha olefins by any conventional method. Particularly preferred starting normal alpha olefins are $C_{14}$ to $C_{40}$ linear olefins are obtained by oligo-polymerization of ethylene, and which contain between 14 and 40, preferably between 18 and 30, and more particularly between 20 and 24 carbon atoms, and wherein the molar proportion of mono alpha olefin is at least 70%.

Specific examples of linear olefins answering to this definition are provided by $C_{16}$ and $C_{18}$ olefins, $C_{14}$ to $C_{16}$, $C_{14}$ to $C_{18}$ and $C_{20}$ to $C_{24}$ olefin cuts, or by combinations of a plurality of these. These olefins are commercially available as AlphaPlus® C20-24 from ChevronPhillips Chemical Company LP. The $C_{14}$ to $C_{40}$ linear mono alpha olefins obtained by direct oligo-polymerization of ethylene, have an infrared absorption spectrum which exhibits an absorption peak at 908 $cm^{-1}$, characteristic of the presence of an ethylene double bond at the end of the chain, on the carbon atoms occupying positions 1 and 2 of the olefin: also distinguished therein are two other absorption peaks at wavelengths of 991 and 1641 $cm^{-1}$. These starting olefins are thereafter isomerized.

As disclosed above, any convenient method can be used to isomerize the normal alpha olefins. In general an isomerization catalyst is required. At least two types of acidic catalysts can be used for isomerization. The acidic catalyst can be solid or liquid. Preferably, the first type of acidic catalyst is a solid catalyst having at least one metal oxide and having an average pore size of less than 5.5 angstroms. More preferably, it is a molecular sieve with a one-dimensional pore system, such as SM-3, MAPO-11, SAPO-11, SSZ-32, ZSM-23, MAPO-39, SAPO-39, ZSM-22 and SSZ-20. Other possible solid acidic catalysts useful for isomerization include ZSM-35, SUZ4, NU-23, NU-87 and natural or synthetic ferrierites. These molecular sieves are well-known in the art and are discussed in Rosemarie Szostak's Handbook of Molecular Sieves (New York, Van Nostrand Reinhold, 1992) and in U.S. Pat. No. 5,282,858, which is hereby incorporated by reference for all purposes. Another type of isomerization catalyst that can be used is iron pentacarbonyl ($Fe(CO)_5$).

The isomerization process may be carried out in batch or continuous mode. The process temperatures can range from 50° C. to 250° C. In the batch mode, a typical method is to use a stirred autoclave or glass flask, which may be heated to the desired reaction temperature. A continuous process is most efficiently carried out in a fixed bed process. (WHSV is the ratio of olefin feed rate in kg/hr to the weight in kg of the catalyst). Space rates in a fixed bed process can range from 0.1 to 10 or more kg olefin/hr/kg catalyst. The space rates can be varied to control the amount of branching in the isomerized olefins. In a fixed bed process, the catalyst is charged to the reactor and activated or dried at a temperature of at least 150° C. under vacuum or flowing inert, dry gas. After activation, the catalyst is cooled to the desired reaction temperature and a flow of the olefin is introduced. The reactor effluent containing the partially branched, isomerized olefin is collected. The resulting partially-branched isomerized olefin contains a different olefin distribution (alpha-olefin, beta-olefin, internal-olefin, trisubstituted olefin and vinylidene-olefin) and branching content than the un-isomerized olefin and conditions are chosen in order to obtain the appropriate structure regarding the level of double bonds between carbon 1 and carbon 2 of the alkyl chain of the olefin (alpha-olefin content).

Persons skilled in the art are able to choose isomerization conditions under which particular levels of isomerization may be achieved. Specifically, the level of isomerization is typically characterized by the amount of alpha olefins and the level of branching in a particular olefin sample or mixture. The amount of alpha olefin and the level of branching can in turn be determined using various conventional methods, including, for example, Fourier Transform Infrared (FTIR)

spectroscopy. In a typical FTIR spectroscopy method, the level (or percentage) of alpha olefins can be measured by following the absorbance of a particular sample at 910 cm$^{-1}$ and comparing it to the 910-cm$^{-1}$ absorbance of calibration samples with known alpha olefin levels. The level (or percentage) of alpha olefin in the calibration samples can be obtained, for example, from $^{13}$C quantitative nuclear magnetic resonance (NMR) spectroscopy according to known protocols.

The percentage of branching can be measured by FTIR spectroscopy by following the absorbance of a sample at 1378 cm$^{-1}$. This absorbance corresponds to the extent of deformation vibration of methyl groups. The absorbance of an isomerized olefin sample is then compared to the 1378-cm$^{-1}$ absorbance of a set of calibration samples with known branching levels. Typically, a particular olefin mix to be tested is first hydrogenated, converting the unbranched portion to n-alkanes and the branched portion to branched alkanes. Gas chromatography is then used to distinguish the unbranched n-alkanes from the branched alkanes, the proportion of which correlates to the percent branching level in that olefin mix.

The isomerized olefin derived from the NAO has less than 25 weight percent residual alpha olefin content, preferably between 0 and 16 weight percent. The branching content of the isomerized olefin is from 15 to 100 weight percent, preferably about 20 to about 40 weight percent, preferably about 20 to about 30 weight percent.

Alkylation Process

In one embodiment of this invention the alkyltoluene used in the invention is directly produced in a single alkylation process. The alkylation process may be any convenient process using an alkylation catalyst. In one embodiment the alkylation catalyst may be a solid catalyst that has at least one metal oxide, which is selected from the group consisting of natural zeolites, synthetic zeolite, synthetic molecular sieves and clays. Preferably, the solid acidic catalyst comprises the acid forms of an acidic clay, or an acidic molecular sieve or a zeolite having an average pore size of at least 6.0 angstroms. Such zeolites include zeolite Y, beta, SSZ-25, SSZ-26 and SSZ-33. Other possible catalysts include L zeolite, mordenite, boggsite, cloverite. VPI-5, MCM-41, MCM-36, SAPO-8, SAPO-5, MAPO-36, SAPO-40, SAPO-41, MAPSO-46, CoAPO-50, hexagonal faujasite, ECM-2, gmelinite, mazzite (omega zeolite), offretite, ZSM-18 and ZSM-12. These catalysts are discussed in Rosemarie Szostak's Handbook of Molecular Sieves (New York, Van Nostrand Reinhold, 1992). More preferably, the solid acidic catalyst comprises zeolite Y. A preferred zeolite Y has a silica to alumina ratio of at least 40:1.

Useful acidic clays may be derived from naturally occurring or synthetic materials. One skilled in the art would realize that there are a number of such clays that are known to be alkylation catalysts. Examples of such acidic clays include montmorillonite, laponite and saponite. Pillared clays may also be used as catalysts.

A particularly preferred catalyst comprises a zeolite Y having a macropore structure wherein the peak macropore diameter of the catalyst, measured by ASTM Test No. D 4284-03, is less than or equal to about 2000 angstroms, and the cumulative pore volume at pore diameters less than or equal to about 500 angstroms, measured by ASTM Test No. D 4284-03, is less than or equal to about 0.30 milliliters per gram, preferably less than about 0.30 milliliters per gram at pore diameters less than or equal to about 400 angstroms, and more preferably in the range of about 0.05 milliliters per gram to about 0.18 milliliters per gram at pore diameters less than or equal to about 400 angstroms. The cumulative pore volume of the zeolite Y catalyst at pore diameters less than or equal to about 300 angstroms is preferably less than about 0.25 milliliters per gram, more preferably at pore diameters less than or equal to about 300 angstroms is less than about 0.20 milliliters per gram, and most preferably at pore diameters less than or equal to about 300 angstroms is in the range of about 0.08 milliliters per gram to about 0.16 milliliters per gram.

Preferably the peak macropore diameter of the zeolite Y catalyst is in the range of about 700 angstroms to about 1800 angstroms, and more preferably the peak macropore diameter is in the range of about 750 angstroms to about 1600 angstroms, and most preferably the peak macropore diameter is in the range of about 800 angstroms to about 1400 angstroms.

The zeolite Y catalyst of the present invention may have silica to alumina ratio of about 5:1 to about 100:1, preferably the silica to alumina ratio is from about 30:1 to about 80:1, and most preferably the silica to alumina ratio is from about 50:1 to about 70:1.

The alkylation reaction is typically carried out with toluene and an isomerized olefin in molar ratios from 1:15 to 25:1. As the olefins have a high boiling point, the process is preferably carried out in the liquid phase. The alkylation process reaction temperature will vary depending upon on the type of catalyst employed. It is generally chosen to result in a high conversion of feed in a short time while preventing undesirable side-reactions or catalyst fouling from occurring. For solid acid catalysts typical alkylation reaction temperatures can range from 85° C. to 250° C., more preferably from 95° C. to 120° C., depending upon the activity of the catalyst; at higher temperatures the amount of light fractions due to cracking is increased. The alkylation process may be carried out in batch or continuous mode.

The presence of water or low molecular weight alcohols such as methanol in the feedstock can have large effects on the activity of the alkylation catalyst. For this reason water or low molecular weight alcohols can be added to the feedstock to control the activity of the alkylation catalyst.

In the batch mode, a typical method is to use a stirred autoclave or glass flask which may be heated to the desired reaction temperature. A continuous process is most efficiently carried out in a fixed bed process.

As disclosed above, the isomer formation of the alkyltoluene may be dependent upon the current activity of the alkylation catalyst and degree of catalyst use or fouling. For example, when the catalyst is fresh or freshly regenerated, and more active, lower feed temperatures are required to obtain the desired isomer distribution. As the catalyst becomes less active, due to fouling and cracking, slightly higher catalyst bed temperature is typically required to obtain the desired isomer distribution of the alkyltoluene.

Monitoring the isomer distribution of the alkyltoluene may be conducted by taking discreet samples at a point after alkylation. Thus for example samples may be taken after the distillation column and analyzed by analytical methods known in the art. A particularly convenient method is through gas chromatograph using a suitable detectors such as flame ionization.

Generally the reactor catalyst bed temperature is controlled by adjusting at least one alkylation process parameter. Alkylation process parameters include for example, alkylation feedstock toluene and olefin temperature, charge mole ratio (CMR) of toluene to olefin, the concentration of polar compounds such as water or low molecular weight alcohols in the feedstock, the weight hourly space velocity of the olefin and/ or the olefin feed superficial velocity.

Olefin feed Superficial Velocity is defined as the flow rate of the olefin divided by the sectional area of catalyst. In a preferred embodiment the olefin feed superficial velocity of is from 25-40 grams/hour/cm$^2$; in a more preferred embodiment the olefin feed superficial velocity is from 25-35 grams/hour/cm$^2$.

The feedstock toluene and olefin temperatures can also be adjusted to arrive at the desired alkylate composition. A convenient method of adjusting temperature is to adjust the temperature using a heat exchanger located between a dehydration column used to remove water from the feedstock and the alkylation reactor. In one embodiment additional cold toluene can be added at this step for further cooling of the feedstock.

The toluene/olefin CMR can also be used to adjust the catalyst bed temperature, and therefore control the isomer distribution. In a preferred embodiment the toluene:olefin CMR is from 8-20; in a more preferred embodiment the toluene:olefin CMR is from 10-20; in a more preferred embodiment from 11-19.

In one embodiment the process of the invention includes developing correlations between the isomer distribution and other process variables such as the temperature in the catalyst bed or the feed temperature, and using these correlations to control the process to achieve the required isomer distribution.

The process conditions are adjusted to maintain the 2-tolyl C24 isomer content below 38 wt % meta content. In one aspect, the process conditions are adjusted to maintain the 2-tolyl C24 isomer content of 18-37 wt % meta-, 20-40 wt % ortho-, and 30-60 wt % para-isomer content. In a further embodiment the meta-isomer content is adjusted to 20-35 wt %; or more preferably to 20-32 wt %; or more preferably to 20-30 wt %. In one embodiment the ortho-isomer content is adjusted to 17-32 wt %; or more preferably to 20-32 wt %; or more preferably to 22-30 wt %. In one embodiment the para-isomer content is adjusted to 35-60 wt %; or more preferably to 40-55 wt %.

In another embodiment of the invention the isomer distributions of at least two alkyltoluenes are measured and blended to provide the isomeric distribution of the invention.

Sulfonation and Neutralization

The next step is the sulfonation of each of the alkyltoluene hydrocarbons or of the mixture of the different alkyl toluene hydrocarbons effected by methods known in themselves, for example by reacting the product of the alkylation step, with concentrated sulfuric acid, with an oleum, with sulfur trioxide dilute in nitrogen or air, or with sulfur trioxide dissolved in sulfur dioxide. This sulfonation reaction can also be effected by contacting the ingredients (alkylate and sulfur trioxide) in the form of a falling film in streams of the same or opposite directions. After sulfonation, the acid or the different sulfonic acids obtained can be purified by conventional methods, such as washing with water or by thermal treatment with stirring by nitrogen bubbling (see, for example, the method described in French patent No 9311709).

The next step of the sulfonic acid or acids with an excess of alkaline earth base can be affected by the addition of an oxide or a hydroxide of alkaline earth metal, such as magnesium, calcium, barium, and particularly lime. Thus, calcium is a particularly preferred alkaline earth metal. The neutralization step may be carried out in dilution oil with an alcohol with a boiling point higher than 80° C. and preferably with a carboxylic acid containing 1 to 4 carbon atoms, in the presence of water, as described in particular in U.S. Pat. No. 4,764,295 incorporated herein by reference in its entirety.

Among the alcohols with boiling points higher than 80° C., linear or branched aliphatic mono alcohols are preferably selected, containing 4 to 10 carbon atoms, such as isobutanol, 2-ethyl hexanol and $C_8$ to $C_{10}$ oxo alcohols. Among the carboxylic acids which can be used are preferably formic acid, acetic acid and their mixtures. Among the dilution oils which are suitable for the neutralization step, are the paraffinic oils such as 100 Neutral oil, as well as naphthenic or mixed oils. After the water and/or alcohol are removed, the solid matter is removed by filtration, and the alkyl toluene sulfonate or sulfonates of alkaline earth metal obtained are collected typically as a concentrate in the added dilution oil.

The term "base number" or "BN" refers to the amount of base equivalent to milligrams of KOH in one gram of sample. Thus, a higher BN reflects more alkaline products and thus a greater alkalinity reserve and thus are characterized by a metal content in excess of that which would be present according to the stoichiometry of the metal cation in the sulfonate. The BN of samples can be determined by a variety of methods, including, for example, ASTM test No. D2896 and other equivalent procedures. The term "total base number" or "TBN" refers to the amount of base equivalent to milligrams of KOH in one gram of the fluid. These terms are often used interchangeably with "base number" or "BN," respectively.

The term "low overbased" refers to a BN or TBN of about 2 to about 60. The alkaline earth metal alkyl toluene sulfonate concentrates of the invention are preferably weakly super alkalinized, that is their total base Number, measured according to Standard Test Method ASTM-D-2896, can range from 2 to 60 mg KOH/g concentrate, preferably 10 to 40 mg KOH/g concentrate, but also from 15 to 25 mg KOH/g concentrate, and they can be used in particular as detergents for lubricating oils.

It is worthwhile to mention that the low BN alkyl toluene sulfonate could be prepared with and without chloride ions and thus be essentially free of chloride ions.

Additional process steps may be employed such as thermal separations for example distillation to remove water or organics or removal of solid substances from the product by filtration or centrifuge or other such methods.

EXAMPLES

The following examples are given as particular embodiments of the invention and to demonstrate the advantages thereof. It is understood that the examples are given by way of illustration and are not intended to limit the specification or the claims that follow in any manner.

Typical Preparation of Neutralized Calcium Sulfonate

The Isomerized Normal Alpha Olefin (NAO)

A $C_{20}$-$C_{24}$ normal alpha olefin was isomerized in accordance with the procedure described in U.S. Pat. No. 5,922,922. $C_{20}$-$C_{24}$ normal alpha olefins typically have compositions similar to the following:
Alpha olefin: 89%
Beta olefin: 0.5%
Internal olefin: 1.4%
Tri-substituted olefin: 0.2%
Vinylidene olefin (determined by Carbon NMR): 9.5%
Branched-chain olefin (determined by infrared spectroscopy): 11%

The resulting isomerized olefins typically have compositions similar to the following:
Alpha olefin: 5.7%
Beta olefin: 33.8%
Internal olefin: 88%

Tri-substituted olefin: 5.8%
Vinylidene olefin (determined by Carbon NMR): 0%
Branched-chain olefin (determined by infra red spectroscopy): 23%.

Synthesis of Alkyltoluene

A fixed bed catalyst alkylation reactor was used for the alkylation. The alkylation catalyst was high crystallinity Y-Zeolite as described in U.S. Pat. No. 7,563,937, incorporated herein by reference in its entirety. After the catalyst was loaded into the reactor and dried using a flow of toluene, the temperature and pressure were set to the desired start-of-run temperature and a pressure of 8 bars, a feed mixture consisting of toluene and the isomerized $C_{20}$-$C_{24}$ normal alpha olefin was introduced in an up-flow manner at the desired molar ratio of toluene to olefin. The olefin feed superficial velocity was about 30 g·h$^{-1}$·cm$^{-2}$ As the feed reached the catalyst in the reactor, alkylation began to occur and internal catalyst bed temperature increased above the inlet temperature. After about 24 hours on-stream, the reactor exotherm was 40° C. and, the olefin conversion in the product was 99%. The run was stopped after 1 week on-stream, although the run could have continued. At this time, the olefin conversion was 99.5%. Following the alkylation step, the excess toluene was distilled from the alkylate product and recycled.

Synthesis of Alkyltoluene Sulfonic Acid

The alkyltoluene produced as described above was sulfonated by a concurrent stream of sulfur trioxide ($SO_3$), produced by the passage of a mixture of oxygen and sulfur dioxide through a catalytic furnace containing vanadium oxide. The sulfur trioxide gas was introduced at the top of a sulfonation reactor (6 meters long and 2.8 cm in diameter or 2 meter long and 0.72 cm of tube spacing) in a concurrent alkylate stream. The resulting sulfonic acid was recovered at the bottom of the reactor. The sulfonation conditions were as follows:

The $SO_3$ loading was 0.64 kg/h·cm for the 6 m long pipe and 0.87 kg/h·cm for the 2 m tube. The alkylates flow rate was adjusted to obtain a $SO_3$:alkylate mole ratio of 0.93. The sulfonation inlet temperature was 50° C.

Dried air was used as vector gas to dilute the $SO_3$ to 4% by volume.

After the sulfonation reaction, the residual sulfuric acid was removed by thermal treatment after dilution by 10% 100N oil, nitrogen bubbling, and stirring at 85° C. until a lower residual $H_2SO_4$ content was obtained (0.5 wt % maximum).

Synthesis of Low Overbased Alkyltoluene Sulfonate

Hydrated lime, diluent oil, 2-Ethylhexanol and a foam inhibitor were placed in a premix vessel or in a reactor and agitated at room temperature for 15 minutes. Water and aqueous calcium chloride were then added to the vessel. The premix was then transferred to the reactor, where a mixture of acetic and formic acid was added to the vessel and agitated. The alkyltoluene sulfonic acid, as prepared above, was added to the reactor over a period of 1 h. During this time, the temperature was increased from ambient temperature to 85° C. Then the mixture was heated up to 100° C. and maintained for 1 hour.

The mixture was then heated to 120° C. and maintained again for 1 hr. The water and alcohol were removed by distillation under vacuum at 185° C. The remaining product was filtered to remove solids from the product.

Low overbased alkyltoluene sulfonate concentrates can be evaluated for gel formation, filtered sediment and filtration rate. These test results, in addition to the analysis of the % meta-, % para- and % ortho-isomer distribution of the alkyltoluene, were obtained by the following methods of measurements:

Gel Formation:

The gel is constituted of product insoluble in naphta or heptanes. It is measured by mixing 25% by weight of product with 75% by weight of heptanes in a glass centrifuge cone. Then the cone is sealed, manually agitated and put in a centrifuge. It is spun for 17 min at 7656 rpm (10000 G). Then the bottom of the cone is examined with a strong light and the volume of sediment accumulated in the nose is determined.

The appearance of the gel is different than the sediment. Sediment is a white and hard solid sticking in the nose of the centrifuge cone, though gel is a soft light brown liquid flowing on the side of the cone when the cone is put up-side down.

Gel can be also observed with the standard test method ASTM D2273. The only difference with the method described above is the dilution with heptanes and the rotation speed of the centrifuge. By experience, when the amount of sediment measured by the ASTM method is higher than 0.2 vol % there is evidence of gel formation in the product.

Filtered Sediment:

ASTM D2273 method, Standard Test Method for Trace Sediment in Lubricating Oils

Filtration Rate:

The filtration rate is the flow rate of product getting out of the filter and is somewhat dependent on the particular apparatus. It is desired to have a stable flow without plugging issue.

Procedure for Determining the Distribution of the Isomers:

A Gas Chromatograph from CE instruments TraceGC2000 (trademark of CE Instruments) with a gas flow regulator fitted with a 30 meter long spiral shape of 250 µm diameter capillary column filled with a stationary phase HP-5 Hewlett Packard 0.25 µm thick (cross-linked 5% phenyl-95% methyl silicone gum) with a FID detector at 320° C.

The vector gas is hydrogen.

The oven temperature profile used was as follows:

| | |
|---|---|
| temp | 60° |
| initial time | 2 mn |
| ramp1 | 40° c./mn |
| final temp1 | 200° |
| final time1 | 0 mn |
| ramp2 | 15° c./mn |
| final temp2 | 320° |
| final time2 | 5 mn |
| ramp3 | off |

In general, the last three peaks that elute from the column for each carbon number alkylate species (i.e. the $C_{20}$ alkylates, the $C_{22}$ alkylates, and the $C_{24}$ alkylates) were the alkyl toluene species in which the alkyl chain was attached at the 2-position along the alkyl chain. The three peaks for each carbon number were the meta, para and ortho-alkyl isomers. The 2-aryl content or 2-tolyl content is defined as the percentage of total monoalkylate (the alkylate species in which one alkyl chain is attached to the aromatic ring) that is comprised of those chemical species in which the attachment of the alkyl chain to the toluene ring is at the 2-position along the alkyl chain.

The isomer distribution was measured on the 2 tolyl $C_{24}$ according to the following equation:

% META 2tolylC24=(area Meta 2tolylC24*100)/
    Σarea (Meta,Para,Ortho 2tolylC24)

% PARA 2tolylC24=(area Para 2tolylC24*100)/Σarea
    (Meta,Para,Ortho 2tolylC24%

% ORTHO 2tolylC24=(area Ortho 2tolylC24*100)/
    Σarea (Meta,Para,Ortho 2tolylC24)

COMPARATIVE EXAMPLES

The alkyltoluenes used in Comparative Examples were made from a commercial process in which the isomeric distributions were not monitored and the alkylation process parameters were not adjusted. The various alkylates were obtained using exactly substantially identical process conditions but at different times in the catalyst life. The CMR of toluene:olefin was 8 in all of these Comparative Examples.

Comparative Example 1

Synthesis of Alkyltoluene Containing an Average of 38% Meta-Isomers

A batch of alkyltoluene was prepared in substantially the same manner as described above (under "Synthesis of Alkyltoluene") with the primary variable being the activity of the catalyst since the alkylation for each batch occurred during different stages in the life cycle of the catalyst.

Specific reaction conditions were as follows: The molar ratio of toluene:olefin was 8; Life of catalyst was about 15% of catalyst life. Thus, the catalyst was relatively active having being 15% spent or having 85% of active life remaining. The alkyltoluene of comparative example 1 contained an average of about 38 wt % meta-isomer content, about 14 wt % ortho-isomer content and about 47 wt % para-isomer content.

Comparative Example 1A-1K

Various process runs (A-K) to manufacture a low overbased calcium sulfonate derived from the alkyltoluene of comparative example 1 were performed at various laboratory, pilot plants and large process plant locations. The sulfonation and overbasing processes as described above were substantially identical at each of the various locations.

TABLE 1

Comparative examples 1A-1K show results of sulfonation and overbasing of the alkyltoluene containing 38 wt % meta-, 14 wt % ortho- and 47 wt % para-isomer content at various locations A-K.

| Comp Ex | % Ca | % CaS | TBN | Gel formation | % Filtered Sediment | Filtration Rate kg/h/m² |
|---|---|---|---|---|---|---|
| Comp 1A | batch not finished | | | Gel | Not measured | Not measured |
| Comp 1B | 2.69 | 1.84 | 24.4 | 3% Gel | >0.2 | Filter plugging |
| Comp 1C | 2.64 | 1.80 | 22.6 | Gel Free | <0.2 | 522 |
| Comp 1D | 2.55 | 1.77 | 21.8 | 3% Gel | >0.2 | 935 |
| Comp 1E | 2.58 | 1.73 | 22.3 | 1% Gel | >0.2 | Filter plugging |
| Comp 1F | 2.57 | 1.77 | 21.8 | 6% Gel | >0.2 | 432 |
| Comp 1G | 2.52 | 1.72 | 21.4 | 0.1% Gel | <0.2 | 53/Filter plugging |
| Comp 1H | 2.67 | 1.81 | 22.9 | Gel | <0.2 | 1520 |
| Comp 1I | 2.52 | 1.75 | 20.8 | 2% Gel | <0.2 | 1085 |

TABLE 1-continued

Comparative examples 1A-1K show results of sulfonation and overbasing of the alkyltoluene containing 38 wt % meta-, 14 wt % ortho- and 47 wt % para-isomer content at various locations A-K.

| Comp Ex | % Ca | % CaS | TBN | Gel formation | % Filtered Sediment | Filtration Rate kg/h/m² |
|---|---|---|---|---|---|---|
| Comp 1J | 2.52 | 1.80 | 20.4 | 0.2% Gel | <0.2 | 515 |
| Comp 1K | 2.54 | 1.74 | 19.9 | 0.2% Gel | <0.2 | 1965 |

As the data show, the majority of the low overbased calcium sulfonates derived from the alkyltoluene of comparative example 1, containing an average of about 38 wt % meta-isomer content, about 14 wt % ortho-isomer content and about 47 wt % para-isomer content contained gel. In some cases the product had filtered sediment contents of >0.2 vol % and demonstrated filter plugging and/or poor filtration rates.

Comparative Example 2

Synthesis of Alkyltoluene Containing an Average of 46 Wt % Meta-Isomers

A batch of alkyltoluene was prepared in substantially the same manner as described above (under "Synthesis of Alkyltoluene"). Specific reaction conditions were as follows: The molar ratio of toluene:olefin was 8; the catalyst used for this trial was freshly regenerated and thus catalyst life can be depicted as ~0.

The alkyltoluene of comparative example 2 contained an average of about 46 wt % meta-isomer content, about 8 wt % ortho-isomer content and about 46 wt % para-isomer content.

Comparative Examples 2A-2E

Various process runs (A-E) to manufacture a low overbased calcium sulfonate derived from the alkyltoluene of comparative example 2 were performed at various laboratory, pilot plants and large process plant locations. The sulfonation and overbasing processes as described above were substantially identical at each of the various locations.

TABLE 2

Comparative examples 2A-2E show results of sulfonation and overbasing of the alkyltoluene containing about 46 wt % meta-isomer content, about 8% ortho-isomer content and about 46 wt % para-isomer content at various locations A-E.

| Comp Ex | % Ca | % CaS | TBN | Gel formation | % Filtered Sediment | Filtration Rate kg/h/m² |
|---|---|---|---|---|---|---|
| Comp 2A | Batch not finished | | | 5% Gel | Not measured | Not measured |
| Comp 2B | Batch not finished | | | 8% Gel | >0.2 | Not measured |
| Comp 2C | 2.48 | 1.73 | 18.5 | 8% Gel | >0.2 | 264 |
| Comp 2D | 2.58 | 1.78 | 20.5 | 4% Gel | >0.2 | 1465 |
| Comp 2E | 2.68 | 1.94 | 19.6 | 3% Gel | >0.2 | Not measured |

As the data show, the low overbased calcium sulfonates derived from the alkyltoluene of comparative example 2, containing an average of about 46 wt % meta-isomer content, about 8 wt % ortho-isomer content and about 46 wt % para-isomer content, contained gel and had a filtered sediment content of >0.2 vol %. In two cases the filter didn't plug but gel was not removed by filtration and thus the amount of sediment in the product was unacceptable

Example 1

Production of Low Meta-Isomer Alkyltoluene Derived from a $C_{20}$-$C_{24}$ Isomerized Normal Alpha Olefin in which Process Parameters were Controlled Batches of alkyltoluene were prepared in substantially the same manner as described above with the following process parameters. The CMR of toluene to olefin and feed flow rate were varied to result in the desired % meta-, para- and % ortho-isomer content. The charge molar ratio of toluene versus olefins was in the range from 11 to 18 as indicated in the Table 1 below as opposed to the CMR of 8:1 in the Comparative Examples. Increasing the charge molar ratio of toluene to olefin provides a supplemental cooling capacity due to the fact that toluene is stored at ambient temperature and in this instance be used to cool down the mixture of toluene and olefins exiting the dehydration column and entering the reactor.

During the trials described below, the distillate condenser was by-passed to avoid heating up toluene, maintaining the temperature of toluene as low as possible to provide better cooling capacity for the feed.

Samples of alkyltoluene were taken all along the trial after the toluene distillation section. The distribution of the isomers was obtained by gas phase chromatography using a 30 m long column.

TABLE 3

Production of alkyltoluene derived from a $C_{20}$-$C_{24}$ isomerized normal alpha olefin using process modifications to control feed temperature.

| Olefin Feed Superficial Velocity ($g \cdot h^{-1} \cdot cm^{-2}$) | Olefin Feed Rate (MT/hr) | CMR (Toluene/ Olefin) | Feed Temp, °C. | Temp in Catalyst Bed, °C. | % meta-isomer | % ortho-isomer | % para-isomer |
|---|---|---|---|---|---|---|---|
| 26.78 | 0.8 | 18 | 72 | — | 26 | 28 | 46 |
| 30.25 | 0.3 | 15 | 72 | 95 | 23 | 31 | 45 |
| 30.63 | 0.6 | 14 | 75 | — | 23 | 31 | 45 |
| 30.22 | 0.5 | 13 | 77 | — | 24 | 31 | 45 |
| 30.22 | 0.5 | 13 | 79 | 106 | 25 | 30 | 45 |
| 30.43 | 0.7 | 12 | 79 | — | 26 | 29 | 45 |
| 30.42 | 0.8 | 11 | 79 | 109 | 27 | 27 | 46 |

As is illustrated in Table 3, desired % meta-, ortho- and para-isomer distribution can be obtained by modifying process conditions such as the charge molar ratio of toluene to olefin or feed flow rate. Life of catalyst was about 20% of catalyst life spent. Thus this catalyst was relatively fresh and active.

Various process runs using alkylated toluene with an isomer distribution of a similar range to that of Example 1 were sulfonated and thereafter neutralized. The low overbased calcium sulfonates derived from the alkyltoluene were performed at various laboratory, pilot plants and large process plant locations. The sulfonation and overbasing processes as described above were substantially identical at each of the various locations. The alkyltoluenes were prepared in a similar fashion as described in the synthesis of alkyltoluene with the isomer distribution conducted post alkylation and thus the process monitoring/adjustment was distinct from Example 1, but thought to be representative of the product produced.

TABLE 4

Effect of isomer distribution content on gel formation of a neutralized calcium alkyltoluene sulfonate

| Example | % meta | % para | % ortho | % cat life | % Ca | % CaS | TBN | Gel formation |
|---|---|---|---|---|---|---|---|---|
| Run 1[1] | 22 | 37 | 40 | 80 | 2.6 | 1.76 | 20.0 | gel free |
| Run 2[2] | 29 | 46 | 25 | 73 | 2.54 | 1.74 | 21.4 | gel free |
| Run 3[3] | 30 | 42 | 27 | 25 | 2.54 | 1.76 | 20.0 | gel free |
| Comp Ex 1 | 38 | 47 | 14 | 15 | 2.58 | 1.77 | 21.8 | 0.1-6% Gel |
| Comp Ex 2 | 46 | 46 | 8 | ~0 | 2.58 | 1.82 | 19.5 | 3-8% Gel |

[1]Average of 10 runs;
[2]Average of 10 runs;
[3]Average of 11 runs

As the data show, the runs to manufacture a low overbased calcium alkyltoluene sulfonate in which the average meta-isomer content is under 38 wt % meta may provide a gel free product and thus improve filtration properties. More particularly, it is shown that a low overbased calcium alkyltoluene sulfonate in which the average meta-isomer content was about 20-35 wt %, para-isomer content was about 35-50 wt %, and ortho-isomer content was about 25-40 wt % of the starting alkyltoluene, did not result in gel formation in the final sulfonate.

Extracting the data from Table 3 it is evident that changes in the alkylation parameters effectuate an isomer distribution and selectivity of the alkyltoluene. Thus by monitoring the isomer distribution and comparing toward a desired distribution set point can lead to adjusting at least one alkylation process parameter in order to provide a target isomer distribution having a 2-tolyl C24 isomer content of less than 38 wt % meta, relative to the total 2-tolyl C24 isomer content. As the tables above display, the filtration properties and more particularly mitigation of soft gel formation of the neutralized calcium alkyltoluene sulfonate can be improved.

What is claimed is:

1. A method for improving filterability in the preparation of an alkaline earth metal alkyltoluene sulfonate concentrate which comprises:
    (a) monitoring the isomeric distribution of at least one alkyltoluene produced by alkylating toluene with an olefin comprising at least one isomerized normal alpha olefin, said isomerized normal alpha olefin having from about 18 to about 30 carbon atoms and having from 15% to 100% branching;
    (b) adjusting at least one alkylation process parameter in order to provide a target isomer distribution having a 2-tolyl C24 isomer content of less than 38% meta, relative to the total 2-tolyl C24 isomer content, wherein the at least one alkylation process parameter is selected from the group consisting of adjusting the feed temperature of at least one reactant, adjusting the charge mole ratio of the reactants, and adjusting the weight hourly space velocity of the feed;

(c) sulfonating the alkyltoluene to produce an alkyltoluene sulfonic acid;

(d) neutralizing the alkyltoluene sulfonic acid with a source of an alkaline earth al to provide a neutralized alkyltoluene sulfonate concentrate having a base number of from about 2 to about 60.

2. The method of claim 1 wherein in step b) the alkylation process parameter comprises reducing the feed temperature of at least one reactant.

3. The method of claim 1 wherein in step b) the alkylation process parameter comprises adjusting the charge mole ratio of the reactants.

4. The method of claim wherein the charge mole ratio of toluene to olefin is from 10-20 to 1.

5. The method of claim 1 wherein in step b) the alkylation process parameter comprises adjusting the weight hourly space velocity of the feed.

6. The method of claim 1, wherein the alkylation process is conducted in a fixed bed catalytic reactor.

7. The method of claim 6, wherein the alkylation process parameter is selected and adjusted to modify a temperature profile in the fixed bed catalytic reactor.

8. The method of claim 6, wherein the catalyst is selected from the group consisting of zeolite Y, SSZ-25, SSZ-26 and SSZ-33.

9. The method of claim 1 wherein the alkylation process parameter is adjusted in order to provide a target isomer distribution having a 2-tolyl C24 isomer content of about 18% to about 37% meta, relative to the total 2-tolyl C24 isomer content.

10. The method of claim 9 wherein the alkylation process parameter is adjusted in order to provide a target isomer distribution having a 2-tolyl C24 isomer content of about 20% to about 30% meta, relative to the total 2-tolyl C24 isomer content.

11. The method of claim 10 wherein the alkylation process parameter is adjusted in order to provide a target isomer distribution having a 2-tolyl C24 isomer content of about 20% to about 45% ortho, relative to the total 2-tolyl C24 isomer content.

12. The method of claim 9 wherein the alkylation process parameter is adjusted in order to provide a target isomer distribution having a 2-tolyl C24 isomer content of about of 20-35% meta-, 25-40% ortho-, and 35-50% para-isomer content relative to the total 2-tolyl C24 isomer content.

13. The method of claim 1 wherein the isomerized normal alpha olefin is characterized as having 20% to about 40% branching.

14. The method of claim 1 wherein the isomerized normal alpha olefin is characterized as having greater than 70 wt % from C20 to C24 carbon atoms.

* * * * *